United States Patent
Rivas (10) Patent No.: US 10,618,045 B2
(45) Date of Patent: Apr. 14, 2020

(54) SENSOR DEVICE WITH BAW RESONATOR AND THROUGH-SUBSTRATE FLUIDIC VIAS

(71) Applicant: Qorvo US, Inc., Greensboro, NC (US)

(72) Inventor: Rio Rivas, Bend, OR (US)

(73) Assignee: Qorvo Biotechnologies, LLC, Plymouth, MN (US)

( * ) Notice: Subject to any disclaimer, the term of this patent is extended or adjusted under 35 U.S.C. 154(b) by 359 days.

(21) Appl. No.: 15/337,338

(22) Filed: Oct. 28, 2016

(65) Prior Publication Data

US 2017/0120242 A1   May 4, 2017

Related U.S. Application Data (60) Provisional application No. 62/247,233, filed on Oct. 28, 2015.

(51) Int. Cl.
*B01L 3/00* (2006.01)
*G01N 29/036* (2006.01)
(Continued)

(52) U.S. Cl.
CPC ........ *B01L 3/50273* (2013.01); *G01N 29/022* (2013.01); *G01N 29/036* (2013.01);
(Continued)

(58) Field of Classification Search
CPC ............. B01L 3/50273; B01L 2200/10; B01L 2300/0645; B01L 2300/0816;
(Continued)

(56) References Cited

U.S. PATENT DOCUMENTS

| 4,640,756 | A | 2/1987 | Wang et al. |
| 6,320,295 | B1 | 11/2001 | McGill et al. |

(Continued)

FOREIGN PATENT DOCUMENTS

| DE | 10 2006 004 448 B3 | 10/2007 |
| WO | WO 2006/063437 A1 | 6/2006 |

(Continued)

OTHER PUBLICATIONS

Xu, Wencheng, et al. "In-liquid quality factor improvement for film bulk acoustic resonators by integration of microfluidic channels." IEEE Electron Device Letters 30.6 (2009): 647-649.*

(Continued)

*Primary Examiner* — Robert J Eom
(74) *Attorney, Agent, or Firm* — Mueting, Raasch & Gebhardt, P.A.

(57) ABSTRACT

A fluidic device incorporating a substrate, at least one bulk acoustic wave (BAW) resonator structure, and a fluidic channel bound at least in part by the at least one BAW resonator structure. The fluidic device further includes at least one fluidic via defined through at least a portion of the substrate, thereby permitting fluidic connections and electrical connections to be provided on opposing upper and lower surfaces of the fluidic device. The at least one BAW resonator structure may include a piezoelectric material comprising a c-axis having an orientation distribution that is predominantly non-parallel to normal of a face of the substrate, and may be overlaid with a functionalization material (e.g., a specific binding material overlying a self-assembled monolayer) to enable detection of a target species in a sample supplied to the fluidic device.

19 Claims, 5 Drawing Sheets

(51) Int. Cl.
   *G01N 29/02* (2006.01)
   *G01N 29/22* (2006.01)
   *G01N 33/543* (2006.01)
   *H03H 9/17* (2006.01)

(52) U.S. Cl.
   CPC ..... *G01N 29/222* (2013.01); *G01N 33/54386* (2013.01); *H03H 9/17* (2013.01); *B01L 2200/10* (2013.01); *B01L 2300/0645* (2013.01); *B01L 2300/0816* (2013.01); *B01L 2300/0887* (2013.01); *B01L 2400/0496* (2013.01); *G01N 2291/0255* (2013.01); *G01N 2291/0256* (2013.01); *G01N 2291/0426* (2013.01); *G01N 2610/00* (2013.01); *H03H 9/175* (2013.01)

(58) Field of Classification Search
   CPC ..... B01L 2300/0887; B01L 2400/0496; G01N 29/022; G01N 29/036; G01N 29/222; G01N 33/54386; G01N 2291/0255; G01N 2291/0256; G01N 2291/0426; G01N 2610/00; H03H 9/17; H03H 9/175
   See application file for complete search history.

(56) References Cited

U.S. PATENT DOCUMENTS

| | | | |
|---|---|---|---|
| 7,468,608 | B2 | 12/2008 | Feucht et al. |
| 7,802,466 | B2 | 9/2010 | Whalen et al. |
| 8,409,875 | B2 | 4/2013 | Johal et al. |
| 9,096,823 | B1 | 8/2015 | Branch et al. |
| 2006/0054941 | A1 | 3/2006 | Lu et al. |
| 2006/0125489 | A1 | 6/2006 | Feucht et al. |
| 2006/0222568 | A1* | 10/2006 | Wang ............ B82Y 15/00 422/70 |
| 2007/0210349 | A1 | 9/2007 | Lu et al. |
| 2010/0088039 | A1 | 4/2010 | Yang et al. |
| 2015/0293060 | A1 | 10/2015 | Jacobsen |
| 2017/0110300 | A1 | 4/2017 | Mccarron et al. |
| 2017/0122911 | A1 | 5/2017 | McCarron et al. |
| 2017/0122936 | A1 | 5/2017 | Rivas et al. |
| 2017/0134002 | A1 | 5/2017 | Rivas et al. |

FOREIGN PATENT DOCUMENTS

| | | |
|---|---|---|
| WO | WO 2007/123539 A1 | 11/2007 |
| WO | PCT/US2016/059312 | 10/2016 |
| WO | PCT/US2016/059327 | 10/2016 |
| WO | PCT/US2016/059677 | 10/2016 |
| WO | WO 2017/075354 A1 | 5/2017 |
| WO | WO 2017/083131 A1 | 5/2017 |

OTHER PUBLICATIONS

Meriam-Webster Definition of "through" https://www.merriam-webster.com/dictionary/through Accessed Aug. 1, 2019.*
Author Unknown, "Laser MicroJet® Technology," Synova: Cool Laser Micro-Machining, Feb. 17, 2015, 8 pages.
Qorvo US, Inc., "Summary of Sales Activity of Predecessor to Applicant Concerning Tilted C-Axis Aluminum Nitride Products," Unpublished, Jan. 10, 2017, 1 page.
Bjurström, J. et al., "Design and Fabrication of Temperature Compensated Liquid FBAR Sensors," IEEE Ultrasonics Symposium, Oct. 2-6, 2006, pp. 894-897.
Chen, Ying-Chung et al., "The Liquid Sensor Using Thin Film Bulk Acoustic Resonator with C-Axis Tilted AlN Films," Journal of Nanomaterials, vol. 2013, Article ID 245095, 2013, 8 pages.
Corso, Christopher et al., "Development of a Simple Inexpensive Bulk Acoustic Wave (BAW) Nanosensor for Cancer Biomarkers: Detection of Secreted Sonic Hedgehog from Prostate Cancer Cells,"
Abstract #8866, Winship Cancer Institute, Emory University, Georgia Institute of Technology, Oct. 2012, 1 page.
Groner, M. D. et al., "Gas diffusion barriers on polymers using $Al_2O_3$ atomic layer deposition," Applied Physics Letters, vol. 88, Jan. 31, 2006, pp. 051907-1 to 051907-3.
Link, Mathias, "Study and realization of shear wave mode solidly mounted film bulk acoustic resonators (FBAR) made of c-axis inclined zinc oxide (ZnO) thin films: application as gravimetric sensors in liquid environments," Université Henri Poincaré—Nancy I, Thesis, Sep. 14, 2006, 225 pages.
Luo, J. K. et al., "Acoustic Wave Based Microfluidics and Lab-on-a-Chip," Modeling and Measurement Methods for Acoustic Waves and for Acoustic Microdevices, Chapter 21, Aug. 28, 2013, InTech, pp. 515-556.
Meyer, Jens et al., "$Al_2O_3/ZrO_2$ Nanolaminates as Ultrahigh Gas-Diffusion Barriers—A Strategy for Reliable Encapsulation of Organic Electronics," Advanced Materials, vol. 21, 2009, pp. 1845-1849.
Milyutin, Evgeny, "Theoretical and Experimental Study of Piezoelectric Modulated AlN Thin Films for Shear Mode BAW Resonators," EPFL, Thesis No. 5113, Nov. 4, 2011, 109 pages.
Munir, Farasat, "A Fast, Scalable Acoustic Resonator-Based Biosensor Array System for Simultaneous Detection of Multiple Biomarkers," Thesis, Georgia Institute of Technology, Dec. 2012, 160 pages.
Nirschl, Martin et al., "CMOS-Integrated Film Bulk Acoustic Resonators for Label-Free Biosensing," Sensors, vol. 10, No. 5, Apr. 27, 2010, pp. 4180-4193.
Yu, Hongyu et al., "Ultra Temperature-Stable Bulk-Acoustic-Wave Resonators with $SiO_2$ Compensation Layer," IEEE Transactions on Ultrasonics, Ferroelectrics, and Frequency Control, vol. 54, No. 10, Oct. 2007, pp. 2102-2109.
Zhou, Yan et al., "Interfacial Structures and Properties of Organic Materials for Biosensors: An Overview," Sensors, vol. 12, Nov. 6, 2012, pp. 15036-15062.
U.S. Appl. No. 62/248,392, filed Oct. 30, 2015, Rivas.
U.S. Appl. No. 62/248,397, filed Oct. 30, 2015, McCarron et al.
U.S. Appl. No. 62/252,688, filed Nov. 9, 2015, Rivas.
U.S. Appl. No. 15/293,063, filed Oct. 13, 2016, McCarron et al.
U.S. Appl. No. 15/337,429, filed Oct. 28, 2016, Rivas et al.
U.S. Appl. No. 15/339,022, filed Oct. 31, 2016, McCarron et al.
U.S. Appl. No. 15/339,062, filed Oct. 31, 2016, Rivas et al.
International Patent Application No. PCT/US2016/059312, filed Oct. 28, 2016; International Search Report / Written Opinion dated Feb. 13, 2017; 12 pages.
International Patent Application No. PCT/US2016/059312, filed Oct. 28, 2016; International Preliminary Report on Patentability dated May 11, 2018; 8 pages.
International Patent Application No. PCT/US2016/059327, filed Oct. 28, 2016; International Search Report / Written Opinion dated Feb. 13, 2017; 15 pages.
International Patent Application No. PCT/US2016/059327, filed Oct. 28, 2016; International Preliminary Report on Patentability dated May 11, 2018; 9 pages.
International Patent Application No. PCT/US2016/059677, filed Oct. 31, 2016; International Search Report / Written Opinion dated May 18, 2017; 11 pages.
International Patent Application No. PCT/US2016/059677, filed Oct. 31, 2016; International Preliminary Report on Patentability dated May 24, 2018; 9 pages.
Chapter 21. Lou et al., "Acoustic Wave Based Microfluidics and Lab-on-a-Chip," in *Modeling and Measurement Methods for Acoustic Waves and for Acoustic Microdevices*. InTech: Aug. 28, 2013. 515-56.
Chen et al., "Characteristics of Dual Mode AlN Thin Film Bulk Acoustic Wave Resonators," May 19-21, 2008, *IEEE International Frequency Control Symposium*, pp. 609-614.
Fan et al., "An adaptive feedback circuit for MEMS resonators," Mar. 1, 2011, *Journal of Micromechanics and Microengineering*, vol. 21; 10 pages.
Fu et al., "Aluminium Nitride thin Film Acoustic Wave Device for Microfluidic and Biosensing Applications," Sep. 1, 2010, *Acoustic Waves*, retrieved on Nov. 14, 2016 from the Internet. Retrieved from the Internet: <URL:https://www/researchgate/net/profile/MPY_Desmulliez/publication/267951195_Aluminium_Nitride_thin_Film- (56) References Cited

OTHER PUBLICATIONS

Acoustin_Wave_Device_for_Microfluidic_and_Biosensing_Applications/links/5450dd8b0cf295b561637e62.pdf, 263-98pgs.
Katardjiev et al., "Recent developments in thin film electro-acoustic technology for biosensor applications," Oct. 19, 2011, *Vacuum*, 86(5):520-31.
"The Laser MicroJet® Technology: A Simple Principle," Synova: Cool Last Micro-Machining, Feb. 17, 2015; 8 pages.
Lee et al., "Microfluidic Mixing: A Review," May 18, 2011, *International Journal of Molecular Sciences*, 12:3263-87.
Miller, "The Stokes-Einstein Law for Diffusion in Solution," *Proceedings of the Royal Society of London. Series A, Containing Papers of a Mathematical and Physical Character (1905-1934)*, Jan. 1924, 106(70):724-49.
Montagut, Yeison et al. "QCM Technology in Biosensors," Biosensors—Emerging Materials and Applications, Chapter 9, 2011, INTECH Open Access Publisher, pp. 153-178.
Nguyen et al., "Micromixers—a review," Dec. 8, 2004, *Journal of Micromechanics and Microengineering*, vol. 15: pp. R1-R16.
Qin et al., "Analytical Study of Dual-Mode Thin Film Bulk Acoustic Resonators (FBARs) Based on ZnO and AlN Films with Tilted C-Axis Orientation," Aug. 2010, *IEEE Transactions on Ultrasonics, Ferroelectrics, and Frequency Control*, 57(8):1840-53.
Rabus et al., "A high sensitivity open loop electronics for gravimetric acoustic wave-based sensors," Jun. 2013, *IEEE Transactions on Ultrasonics, Ferroelectrics, and Frequency Control*, 60(6):1219-1226.
Ramakrishnan, et al., "Resonant Frequency Characteristics of a SAW Device Attached to Resonating Micropillars," 2012, *Sensors*, 12(4):3789-97.
Stroock et al., "Chaotic Mixer for Microchannels," Jan. 25, 2002, *Science*, vol. 295: pp. 647-651.
Suh et al., "A Review on Mixing in Microfluidics," Sep. 30, 2010, *Micromachines*, 1(3):82-111.
Through Silicon Vias (TSV) for backside electrical connection are common in devices https://en.wikipedia.org/wiki/Through-silicon_via.
Voiculescu et al., "Acoustic wave based MEMS devices for biosensing applications," Dec. 21, 2011, *Biosensors and Bioelectronics*, 33(1):1-9.
Wingqvist et al., "Shear mode AlN thin film electro-acoustic resonant sensor operation in viscous media," Mar. 30, 2007, *International Journal Devoted to Research and Development of Physical and Chemical Transducers: Sensors and Actuator B Chemical*, 123(1):466-73.
Zhang et al., "A Microfluidic Love-Wave Biosensing Device for PSA Detection Based on an Aptamer Beacon Probe," 2015, *Sensors*, 15:13839-850.
Zhang et al., "A single-chip biosensing platform integrating FBAR sensor with digital microfluidic device," IEEE International Ultrasonics Symposium Proceedings, (IEEE) Tianjin, China, Sep. 3, 2014. pp. 1521-1523.

\* cited by examiner

SENSOR DEVICE WITH BAW RESONATOR AND THROUGH-SUBSTRATE FLUIDIC VIAS

STATEMENT OF RELATED APPLICATIONS

This application is a non-provisional of U.S. provisional patent application Ser. No. 62/247,233, filed Oct. 28, 2015, the disclosure of which is hereby incorporated herein by reference in its entirety. Subject matter disclosed herein also relates to U.S. patent application Ser. No. 15/337,429 entitled "Fluidic Device Including BAW Resonators Along Opposing Channel Surfaces" filed or on Oct. 28, 2016, the contents of which are hereby incorporated by reference as if set forth fully herein.

TECHNICAL FIELD

The present disclosure relates to acoustic resonator devices, including acoustic wave sensors and microfluidic devices suitable for biosensing or biochemical sensing applications.

BACKGROUND

A biosensor (or biological sensor) is an analytical device including a biological element and a transducer that converts a biological response into an electrical signal. Certain biosensors involve a selective biochemical reaction between a specific binding material (e.g., an antibody, a receptor, a ligand, etc.) and a target species (e.g., molecule, protein, DNA, virus, bacteria, etc.), and the product of this highly specific reaction is converted into a measurable quantity by a transducer. Other sensors may utilize a non-specific binding material capable of binding multiple types or classes of molecules or other moieties that may be present in a sample, such as may be useful in chemical sensing applications. The term "functionalization material" may be used herein to generally relate to both specific and non-specific binding materials. Transduction methods may be based on various principles, such as electrochemical, optical, electrical, acoustic, and so on. Among these, acoustic transduction offers a number of potential advantages, such as being real time, label-free, and low cost, as well as exhibiting high sensitivity.

An acoustic wave device employs an acoustic wave that propagates through or on the surface of a piezoelectric material, whereby any changes to the characteristics of the propagation path affect the velocity and/or amplitude of the wave. Presence of functionalization material embodied in a specific binding material along an active region of an acoustic wave device permits a specific analyte to be bound to the specific binding material, thereby altering the mass being vibrated by the acoustic wave and altering the wave propagation characteristics (e.g., velocity, thereby altering resonance frequency). Changes in velocity can be monitored by measuring the frequency, magnitude, or phase characteristics of the sensor (e.g., frequency shift), and can be correlated to a physical quantity being measured.

In the case of a piezoelectric crystal resonator, an acoustic wave may embody either a bulk acoustic wave (BAW) propagating through the interior of a piezoelectric material, or a surface acoustic wave (SAW) propagating on the surface of the piezoelectric material. SAW devices involve transduction of acoustic waves (commonly including two-dimensional Rayleigh waves) utilizing interdigital transducers along the surface of a piezoelectric material, with the waves being confined to a penetration depth of about one wavelength. In a BAW device, three wave modes can propagate, namely, one longitudinal mode (embodying longitudinal waves, also called compressional/extensional waves), and two shear modes (embodying shear waves, also called transverse waves), with longitudinal and shear modes respectively identifying vibrations where particle motion is parallel to or perpendicular to the direction of wave propagation. The longitudinal mode is characterized by compression and elongation in the direction of the propagation, whereas the shear modes consist of motion perpendicular to the direction of propagation with no local change of volume. Longitudinal and shear modes propagate at different velocities. In practice, these modes are not necessarily pure modes as the particle vibration, or polarization, is neither purely parallel nor purely perpendicular to the propagation direction. The propagation characteristics of the respective modes depend on the material properties and propagation direction respective to the crystal axis orientations. Since shear waves exhibit a very low penetration depth into a liquid, a device with pure or predominant shear modes can operate in liquids without significant radiation losses (in contrast with longitudinal waves, which can be radiated in liquid and exhibit significant propagation losses). Restated, shear mode vibrations are beneficial for operation of acoustic wave devices with fluids (e.g., liquids) because shear waves do not impart significant energy into fluids.

Certain piezoelectric thin films are capable of exciting both longitudinal and shear mode resonance, such as hexagonal crystal structure piezoelectric materials including (but not limited to) aluminum nitride [AlN] and zinc oxide [ZnO]. To excite a wave including a shear mode using a piezoelectric material arranged between electrodes, a polarization axis in a piezoelectric thin film must generally be non-perpendicular to (e.g., tilted relative to) the film plane. Hexagonal crystal structure piezoelectric materials such as aluminum nitride (AlN) and zinc oxide (ZnO) tend to develop their polarization axis (i.e., c-axis) perpendicular to the film plane, but may be grown by known techniques (e.g., reactive radio frequency magnetron sputtering) to yield crystals (e.g., at least over a small area) with a c-axis having an orientation distribution that is predominantly non-parallel to normal of a face of the substrate. In biological sensing applications involving liquid media, the shear component of the resonator is used. In such applications, piezoelectric material may be grown with a c-axis orientation distribution that is non-perpendicular relative to a face of an underlying substrate to enable a BAW resonator structure to exhibit a dominant shear response upon application of an alternating current signal across electrodes thereof.

Typically, BAW devices are fabricated by micro-electromechanical systems (MEMS) fabrication techniques owing to the need to provide microscale features suitable for facilitating high frequency operation. In the context of biosensors, functionalization materials (e.g., specific binding materials; also known as bioactive probes or agents) may be deposited on sensor surfaces by various techniques, such as microarray spotting (also known as microarray printing). Functionalization materials providing non-specific binding utility (e.g., permitting binding of multiple types or species of molecules) may also be used in certain contexts, such as chemical sensing.

Biochemical sensors may incorporate multiple resonators, such as at least one reference region devoid of specific binding material as well as one or more sensing regions (optionally arranged in one-dimensional or two-dimensional arrays) including one or more specific binding materials. Presence of multiple resonators as well as fluidic connections presents packaging constraints that tend to increase the size and cost of sensor devices, due to the need to provide multiple electrical and fluidic connections. Such devices also entail a reliability risk due to the presence of electrical connections and fluidic connections proximate to one another. For example, acoustic resonators frequently utilize electrodes composed of reactive metals (e.g., aluminum or aluminum alloy) that are susceptible to corrosion when contacted with liquid. Unintended contact of fluid with bond pads of an acoustic resonator can result in damage to or reduced reliability of top side metal traces.

Accordingly, there is a need for devices incorporating bulk acoustic wave resonator structures suitable for operation in the presence of liquid for biosensing or biochemical sensing applications that overcome limitations associated with conventional devices.

SUMMARY

The present disclosure provides a fluidic device incorporating at least one acoustic resonator with fluidic vias defined through a substrate. More specifically, the present disclosure provides a fluidic device incorporating a base structure including a substrate, at least one bulk acoustic wave (BAW) resonator structure arranged over at least a portion of the substrate, and a functionalization material arranged over at least a portion of an active region, with at least one fluidic via defined through at least a portion of the base structure (e.g., extending through at least the substrate) to provide fluid communication with a fluidic channel overlying and/or bounded at least in part by the base structure. Such a configuration permits electrical and fluid connections to a fluidic device to be separated from one another on different surfaces (e.g., with electrical connections arranged along an upper or top surface of the fluidic device, and fluidic connections arranged along a lower or bottom surface of the fluidic device). This configuration enables reduction in the size and cost of a fluidic device incorporating at least one bulk acoustic wave resonator structure, and promotes improved reliability of such a device. In certain embodiments, the functionalization material may embody a specific binding material; in other embodiments, the functionalization material may comprise a non-specific binding material.

In one aspect, a fluidic device comprises: a base structure comprising (i) a substrate; (ii) at least one bulk acoustic wave resonator structure arranged over at least a portion of the substrate, the at least one bulk acoustic wave resonator structure including a piezoelectric material comprising a c-axis having an orientation distribution that is predominantly non-parallel to normal of a face of the substrate, a top side electrode arranged over a portion of the piezoelectric material, and a bottom side electrode arranged between the piezoelectric material and the substrate, wherein a portion of the piezoelectric material is arranged between the top side electrode and the bottom side electrode to form an active region; and (iii) a functionalization material arranged over at least a portion of the active region; a fluidic channel bounded at least in part by the base structure; and at least one fluidic via defined through at least a portion of the base structure including the substrate and in fluid communication with the fluidic channel.

In certain embodiments, the base structure further comprises a self-assembled monolayer arranged over the active region, wherein the functionalization material comprises a specific binding material arranged over the self-assembled monolayer.

In certain embodiments, the base structure further comprises an interface layer arranged over at least a portion of the active region, and the self-assembled monolayer is arranged over at least a portion of the interface layer. In certain embodiments, the interface layer extends over less than an entirety of the piezoelectric material. In certain embodiments, the top side electrode comprises a non-noble metal, and the fluidic device further comprises a hermeticity layer arranged between the interface layer and the top side electrode.

In certain embodiments, the fluidic device further comprises at least one channel boundary-defining structure arranged over the base structure, wherein the at least one channel boundary-defining structure defines an upper boundary and at least one lateral boundary of the fluidic channel.

In certain embodiments, the at least one channel boundary-defining structure comprises at least one intermediate structure defining the at least one lateral boundary of the fluidic channel, and comprises a cover defining the upper boundary of the fluidic channel.

In certain embodiments, the at least one fluidic via extends through the substrate and the piezoelectric material. In certain embodiments, the at least one fluidic via comprises a plurality of fluidic vias defined through the at least a portion of the base structure. In certain embodiments, the at least one fluidic via extends through the substrate, the acoustic reflector structure, and the piezoelectric material.

In certain embodiments, the base structure further comprises an acoustic reflector structure arranged between the substrate and the bottom side electrode.

In certain embodiments, the substrate defines a recess underlying the bottom side electrode and proximate to the active region. In certain embodiments, the base structure further comprises a support layer arranged between the recess defined in the substrate and at least a portion of the bottom side electrode.

In certain embodiments, the at least one bulk acoustic wave resonator structure comprises a plurality of bulk acoustic wave resonator structures registered with the fluidic channel.

In certain embodiments, the functionalization material comprises a non-specific binding material.

In certain embodiments, the fluidic device further comprises a top side arranged closer to the piezoelectric material than to the substrate; a bottom side arranged closer to the substrate than to the piezoelectric material; and a first electrical bond pad and a second electrical bond pad arranged along the top side, wherein the first electrical bond pad is in conductive electrical communication with the top side electrode, and the second electrical bond pad is in conductive electrical communication with the bottom side electrode; wherein the at least one fluidic via extends through the bottom side.

In certain embodiments, a method for biological or chemical sensing comprises: supplying a fluid containing a target species through the at least one fluidic via into the fluidic channel of a fluidic device disclosed herein, wherein said supplying is configured to cause at least some of the target species to bind to functionalization material; inducing a bulk acoustic wave in the active region; and sensing at change in at least one of a frequency property, a magnitude property, or a phase property of the at least one bulk acoustic wave resonator structure to indicate at least one of presence or quantity of target species bound to the functionalization material.

In another aspect, a method for fabricating a fluidic device comprising at least one bulk acoustic wave resonator structure arranged over at least a portion of a substrate, the at least one bulk acoustic wave resonator structure including a piezoelectric material comprising a c-axis having an orientation distribution that is predominantly non-parallel to normal of a face of the substrate, a top side electrode arranged over a portion of the piezoelectric material, and a bottom side electrode arranged between the piezoelectric material and the substrate, wherein a portion of the piezoelectric material is arranged between the top side electrode and the bottom side electrode to form an active region, comprises: defining at least one fluidic via through the substrate and the piezoelectric material; providing at least one functionalization material over at least a portion of the active region; and arranging at least one channel boundary-defining structure over the at least one bulk acoustic wave resonator structure, wherein the at least one channel boundary-defining structure defines an upper boundary and at least one lateral boundary of a fluidic channel in fluidic communication with the at least one fluidic via, and the active region is arranged along a portion of a lower boundary of the fluidic channel.

In certain embodiments, the method further includes forming an interface layer over at least a portion of the active region, forming a self-assembled monolayer over at least a portion of the interface layer, and providing at least one functionalization material over at least a portion of the self-assembled monolayer, wherein the at least one functionalization material comprises a specific binding material. In certain embodiments, the method further includes forming a hermeticity layer over the top side electrode prior to the forming of the interface layer over at least a portion of the active region.

In certain embodiments, the defining of the at least one fluidic via through the substrate and the piezoelectric material comprises laser micromachining guided in a water jet.

In certain embodiments, the arranging of the at least one channel boundary-defining structure over the at least one bulk acoustic wave resonator structure is performed prior to the providing of the at least one functionalization material over at least a portion of the active region.

In another aspect, any of the foregoing aspects, and/or various separate aspects and features as described herein, may be combined for additional advantage. Any of the various features and elements as disclosed herein may be combined with one or more other disclosed features and elements unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the disclosure, and together with the description serve to explain the principles of the disclosure.

DETAILED DESCRIPTION

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It should be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It should also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It should be understood that, although the terms "upper," "lower," "bottom," "intermediate," "middle," "top," and the like may be used herein to describe various elements, these elements should not be limited by these terms. These terms are only used to distinguish one element from another. For example, a first element could be termed an "upper" element and, similarly, a second element could be termed an "upper" element depending on the relative orientations of these elements, without departing from the scope of the present disclosure.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having meanings that are consistent with their meanings in the context of this specification and the relevant art and will not be interpreted in an idealized or overly formal sense unless expressly so defined herein.

The present disclosure relates in one aspect to a fluidic device comprising a base structure including a substrate, at least one bulk acoustic wave (BAW) resonator structure arranged over at least a portion of the substrate, and a functionalization material (e.g., at least one specific binding material) arranged over at least a portion of an active region of the at least one bulk acoustic wave resonator structure, wherein a fluidic channel is bounded at least in part by the base structure, and at least one fluidic via is defined through at least a portion of the base structure. In certain embodiments, a functionalization material embodied in a specific binding material may be provided over an underlying self-assembled monolayer (SAM) that is arranged over an interface layer. The BAW resonator structure includes a piezoelectric material, a top side electrode arranged over a portion of the piezoelectric material, and a bottom side electrode arranged between the piezoelectric material and the substrate. The active region comprises a portion of the piezoelectric material arranged between the top side electrode and the bottom side electrode. In certain embodiments, a top side electrode may be formed of, or plated with, gold or another noble metal, such that an appropriate (e.g., thiol-based) SAM may be attached directly to the noble metal surface. In other embodiments, a top side electrode comprising a material (e.g., aluminum or aluminum alloy) other than a noble metal may be overlaid with an interface layer suitable for attachment of an organosilane-based SAM, optionally in combination with a hermeticity layer arranged between the top side electrode and the interface layer.

By providing at least one fluidic via (e.g., fluidic conduit) extending through at least a portion of the base structure (e.g., including but not limited to the substrate), and fluidic ports (which may be located on a back or bottom side of the base structure) for supplying fluid to the fluidic channel, electrical connections arranged on the front side of the fluidic device are spaced apart and isolated from a fluid source. In this manner, electrical and fluid connections may be provided on different (e.g., opposing) upper and lower surfaces of a fluidic device. For example, in certain embodiments, a fluid inlet port and a fluid outlet port are arranged on a lower or bottom side of a fluidic device, and electrical connections (e.g., electrical bond pads) are provided on an upper or top side of the fluidic device. This configuration enables a reduction in size and cost of a fluidic device incorporating one or more BAW resonator structures, and avoids the potential for liquid to inadvertently contact electrical connections of the fluidic device.

In certain embodiments, less than an entirety of the piezoelectric material of a BAW resonator structure of a fluidic device described herein is overlaid with an interface layer that is available to receive a self-assembled monolayer (SAM). In certain embodiments, the interface layer is arranged over less than an entirety of the piezoelectric material; or, alternatively, an interface layer may be arranged over substantially the entirety of a piezoelectric material, while a patterned blocking layer (e.g., at least one of $Si_3N_4$, SiC, photoresist (e.g., SU-8), polyimide, parylene, or poly (ethylene glycol)) is arranged over at least a portion of the interface layer, whereby presence of the patterned blocking material renders a portion of the interface layer unavailable to receive a SAM. Deposition techniques such as atomic layer deposition (ALD), chemical vapor deposition (CVD), or physical vapor deposition (PVD) may be used in conjunction with one or more masks (e.g., photolithographic masks) to pattern the interface layer over selected portions (i.e., less than the entirety) of a MEMS resonator device, including at least a portion of an active region. In certain embodiments, the interface layer comprises a hydroxylated oxide surface, and the self-assembled monolayer comprises an organosilane material. In certain embodiments, the interface layer comprises gold or another noble metal, and the self-assembled monolayer comprises a thiol material. Following formation of an interface layer, a SAM may be formed thereover, and a functionalization (e.g., specific binding) material may be applied to the SAM. Preferably, specific binding material is registered with at least a portion of an active region of a BAW resonator structure.

Figure 1:
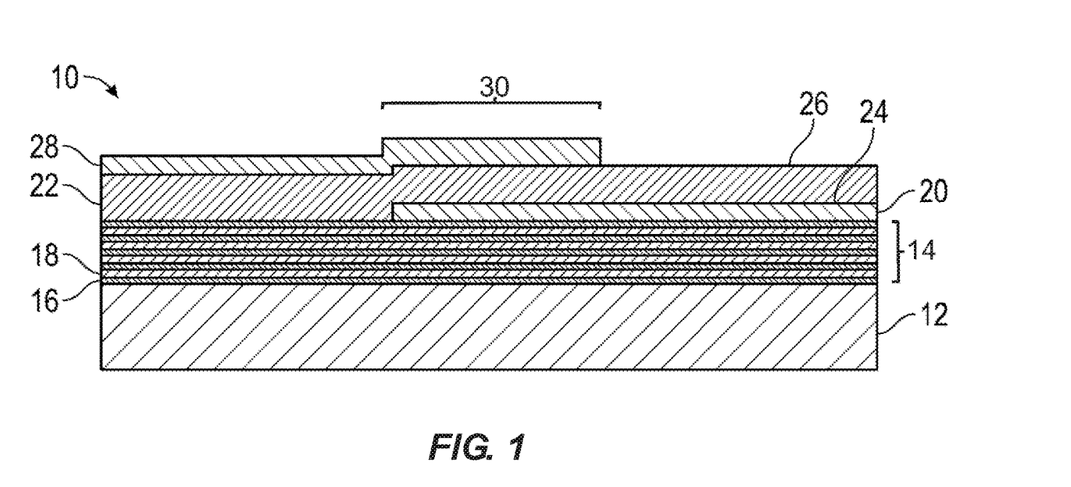
FIG. 1 is a schematic cross-sectional view of a portion of a bulk acoustic wave (BAW) MEMS resonator device that is devoid of overlying layers and fluidic vias but useable with embodiments disclosed herein.

FIG. 1 is a schematic cross-sectional view of a portion of a bulk acoustic wave MEMS resonator device 10 that is devoid of overlying layers and fluidic vias, but is useful to introduce features of embodiments to be disclosed hereinafter. The bulk acoustic wave MEMS resonator device 10 includes a substrate 12 (e.g., typically silicon or another semiconductor material), an acoustic reflector 14 arranged over the substrate 12, a piezoelectric material 22, and bottom and top side electrodes 20, 28. The bottom side electrode 20 is arranged along a portion of a lower surface 24 of the piezoelectric material 22 (between the acoustic reflector 14 and the piezoelectric material 22), and the top side electrode 28 is arranged along a portion of an upper surface 26 of the piezoelectric material 22. An area in which the piezoelectric material 22 is arranged between overlapping portions of the top side electrode 28 and the bottom side electrode 20 is considered an active region 30 of the resonator device 10. The acoustic reflector 14 serves to reflect acoustic waves and therefore reduce or avoid their dissipation in the substrate 12. In certain embodiments, an acoustic reflector 14 includes alternating thin layers 16, 18 of different materials (e.g., silicon oxicarbide [SiOC], silicon nitride [$Si_3N_4$], silicon dioxide [$SiO_2$], aluminum nitride [AlN], tungsten [W], and molybdenum [Mo]), optionally embodied in a quarter-wave Bragg mirror, deposited over the substrate 12. In certain embodiments, other types of acoustic reflectors may be used. Steps for forming the resonator device 10 may include depositing the acoustic reflector 14 over the substrate 12, followed by deposition of the bottom side electrode 20, followed by growth (e.g., via sputtering or other appropriate methods) of the piezoelectric material 22, followed by deposition of the top side electrode 28.

In certain embodiments, an interface layer is patterned or otherwise available to receive a SAM over an entirety of an active region of a MEMS resonator device, to permit a SAM and functionalization (e.g., specific binding) material to be applied over the interface layer to overlap the entire active region. In other embodiments, a blocking layer may be patterned over an interface layer, or only a portion of the interface layer may be otherwise available to receive a SAM, over only a portion of an active region, to permit the SAM and functionalization material applied over the interface layer to overlap only a portion of the active region.

In certain embodiments, photolithography may be used to promote patterning of interface material or blocking material over portions of a MEMS resonator device. Photolithography involves use of light to transfer a geometric pattern from a photomask to a light-sensitive chemical photoresist on a substrate, and is a process well known to those of ordinary skill in the semiconductor fabrication art. Typical steps employed in photolithography include wafer cleaning, photoresist application (involving either positive or negative photoresist), mask alignment, and exposure and development. After features are defined in photoresist on a desired surface, an interface layer may be patterned by etching in one or more gaps in a photoresist layer, and the photoresist layer may be subsequently removed (e.g., using a liquid photoresist stripper, by ashing via application of an oxygen-containing plasma, or another removal process).

In certain embodiments, an interface layer (e.g., arrangeable between a top side electrode and a SAM) includes a hydroxylated oxide surface suitable for formation of an organosilane SAM. A preferred interface layer material including a hydroxylated oxide surface is silicon dioxide [$SiO_2$]. Alternative materials incorporating hydroxylated oxide surfaces for forming interface layers include titanium dioxide [$TiO_2$], tantalum pentoxide [$Ta_2O_5$], hafnium oxide [$HfO_2$], or aluminum oxide [$Al_2O_3$]. Other alternative materials incorporating hydroxylated oxide surfaces will be known to those skilled in the art, and these alternatives are considered to be within the scope of the present disclosure.

In other embodiments, an interface layer (e.g., arrangeable between a top side electrode and a SAM), or at least one electrode that is devoid of an overlying interface layer, includes gold or another noble metal (e.g., ruthenium, rhodium, palladium, osmium, iridium, platinum, or silver) suitable for receiving a thiol-based SAM.

In certain embodiments incorporating electrode materials subject to corrosion, a hermeticity layer may also be applied between a top side electrode and an interface layer. A hermeticity layer may be unnecessary when noble metals (e.g., gold, platinum, etc.) are used for top side electrodes. If provided, a hermeticity layer preferably includes a dielectric material with a low water vapor transmission rate (e.g., no greater than 0.1 (g/m$^2$/day)). Following deposition of a hermeticity layer and an interface layer, a SAM may be formed over the interface layer, with the SAM including an organosilane material in certain embodiments. The hermeticity layer protects a reactive electrode material (e.g., aluminum or aluminum alloy) from attack in corrosive liquid environments, and the interface layer facilitates proper chemical binding of the SAM.

In certain embodiments, a hermeticity layer and/or an interface layer may be applied via one or more deposition processes such as atomic layer deposition (ALD), chemical vapor deposition (CVD), or physical vapor deposition (PVD). Of the foregoing processes, ALD is preferred for deposition of at least the hermeticity layer (and may also be preferable for deposition of the interface layer), due to its ability to provide excellent conformal coating with good step coverage over device features, so as to provide layer structures that are free of pinholes. Moreover, ALD is capable of forming uniformly thin layers that provide relatively little damping of acoustic vibrations that would otherwise result in degraded device performance. Adequacy of coverage is important for a hermeticity layer (if present) to avoid corrosion of the underlying electrode. If ALD is used for deposition of a hermeticity layer, then in certain embodiments a hermeticity layer may include a thickness in a range of from about 10 nm to about 25 nm. In certain embodiments, hermeticity layer thickness is about 15 nm, or from about 12 nm to about 18 nm. Conversely, if another process such as CVD is used, then a hermeticity layer may include a thickness in a range of from about 80 nm to about 150 nm or more, or in a range of from about 80 nm to about 120 nm. Considering both of the foregoing processes, hermeticity layer thicknesses may range from about 5 nm to about 150 nm. If ALD is used for deposition of an interface layer, then an interface layer may include a thickness in a range of from about 5 nm to about 15 nm. In certain embodiments, an interface layer may include a thickness of about 10 nm, or in a range of from about 8 nm to about 12 nm. Other interface layer thickness ranges and/or deposition techniques other than ALD may be used in certain embodiments. In certain embodiments, a hermeticity layer and an interface layer may be sequentially applied in a vacuum environment, thereby promoting a high-quality interface between the two layers.

If provided, a hermeticity layer may include an oxide, a nitride, or an oxynitride material serving as a dielectric material and having a low water vapor transmission rate (e.g., no greater than 0.1 (g/m$^2$/day)) according to certain embodiments. In certain embodiments, a hermeticity layer includes at least one of $Al_2O_3$ or SiN. In certain embodiments, an interface layer includes at least one of $SiO_2$, $TiO_2$, or $Ta_2O_5$. In certain embodiments, multiple materials may be combined in a single hermeticity layer, and/or a hermeticity layer may include multiple sublayers of different materials. Preferably, a hermeticity layer is further selected to promote compatibility with an underlying reactive metal (e.g., aluminum or aluminum alloy) electrode structure of an acoustic resonator structure. Although aluminum or aluminum alloys are frequently used as electrode materials in bulk acoustic wave resonator structures, various transition and post-transition metals can be used for such electrodes.

Following deposition of an interface layer (optionally arranged over an underlying hermeticity layer), a SAM is preferably formed over the interface layer. SAMs are typically formed by exposure of a solid surface to amphiphilic molecules with chemical groups that exhibit strong affinities for the solid surface. When an interface layer comprising a hydroxylated oxide surface is used, then organosilane SAMs are particularly preferred for attachment to the hydroxylated oxide surface. Organosilane SAMs promote surface bonding through silicon-oxygen (Si—O) bonds. More specifically, organosilane molecules include a hydrolytically sensitive group and an organic group, and are therefore useful for coupling inorganic materials to organic polymers. An organosilane SAM may be formed by exposing a hydroxylated surface to an organosilane material in the presence of trace amounts of water to form intermediate silanol groups. These groups then react with free hydroxyl groups on the hydroxylated surface to covalently immobilize the organosilane. Examples of possible organosilane-based SAMs that are compatible with interface layers incorporating hydroxylated oxide surfaces include 3-glycidoxypropyltrimethoxysilane (GPTMS), 3-mercaptopropyltrimethoxysilane (MPTMS), 3-aminopropyltrimethoxysilane (APTMS), and octadecyltrimethoxysilane (OTMS), including their ethoxy- and chloro-variants. Additional silanes that may be used for SAMs include poly(ethylene glycol) (PEG) conjugated variants. Those skilled in the art will recognize that other alternatives exist, and these alternatives are considered to be within the scope of the present disclosure. An exemplary SAM may include a thickness in a range of at least 0.5 nm or more. Preferably, a SAM readily binds to the locally patterned interface layer, but does not readily bind to other adjacent material layers (e.g., a hermeticity layer, a piezoelectric material, and/or a blocking material layer).

When an electrode(s) and/or interface layer comprising gold or another noble metal is used, then thiol-based (e.g., alkanethiol-based) SAMs may be used. Alkanethiols are molecules with an alkyl chain as the back bone, a tail group, and an S—H head group. Thiols may be used on noble metal interface layers due to the strong affinity of sulfur for these metals. Examples of thiol-based SAMs that may be used include, but are not limited to, 1-dodecanethiol (DDT), 11-mercaptoundecanoic acid (MUA), and hydroxyl-terminated (hexaethylene glycol) undecanethiol (1-UDT). These thiols contain the same backbone, but different end groups—namely, methyl ($CH_3$), carboxyl (COOH), and hydroxyl-terminated hexaethylene glycol (HO—$(CH_2CH_2O)_6$) for DDT, MUA, and 1-UDT, respectively. In certain embodiments, SAMs may be formed by incubating gold surfaces in thiol solutions using a suitable solvent, such as anhydrous ethanol.

Following formation of a SAM, the SAM may be biologically functionalized, such by receiving at least one functionalization (e.g., specific binding) material. In certain embodiments, specific binding materials may be applied on or over a SAM using a microarray spotting needle or other suitable methods. In certain embodiments, an interface layer may be patterned (e.g., using photolithography and selective etching for defining the interface layer) with a high dimensional tolerance over only a portion of a resonator structure (which includes a substrate), a SAM may be applied over the interface layer, and a subsequently applied specific binding material attaches only to the SAM. In certain embodiments, patterning of an interface layer may provide a higher dimensional tolerance for positioning of the specific binding material than could be attained by microarray spotting alone. Examples of specific binding materials include, but are not limited to, antibodies, receptors, ligands, and the like. A specific binding material is preferably configured to receive a predefined target species (e.g., molecule, protein, DNA, virus, bacteria, etc.). Functionalization material including specific binding material may include a thickness in a range of from about 5 nm to about 1000 nm, or from about 5 nm to about 500 nm. In certain embodiments, an array of different specific binding materials may be provided over different active areas of a multi-resonator device (i.e., a resonator device including multiple active areas), optionally in combination with one or more active areas that are devoid of specific binding materials to serve as comparison (or "reference") regions. In certain embodiments, a functionalization material may provide non-specific binding utility.

Figure 2:
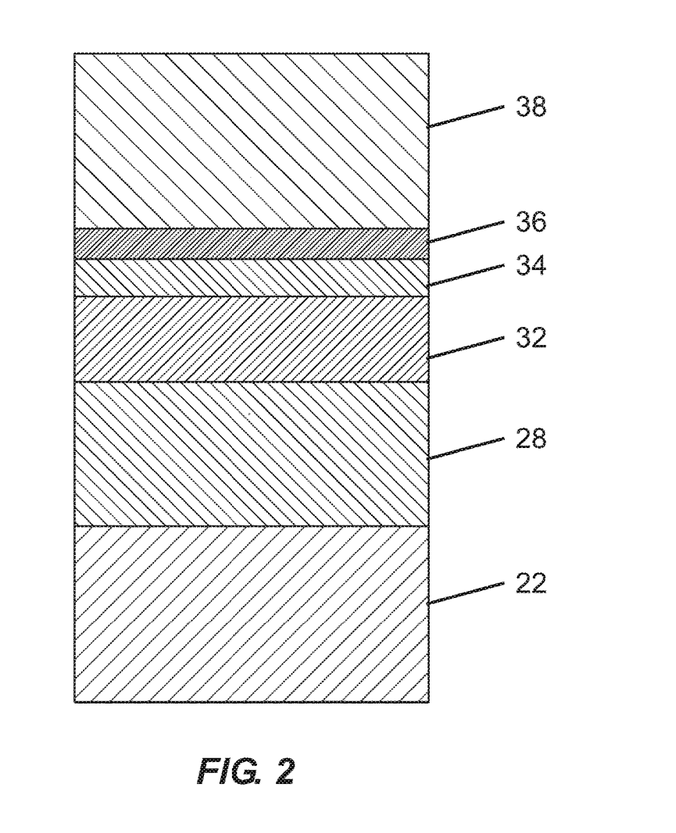
FIG. 2 is a schematic cross-sectional view of an upper portion of a bulk acoustic wave MEMS resonator device including a piezoelectric material and a top side electrode overlaid with a hermeticity layer, an interface layer, a self-assembled monolayer, and functionalization (e.g., specific binding) material.

An example of a bulk acoustic wave MEMS resonator device overlaid with multiple layers to provide biosensing utility, and useable with fluidic devices according to certain embodiments, is provided in FIG. 2. FIG. 2 is a schematic cross-sectional view of an upper portion of a bulk acoustic wave MEMS resonator device including a piezoelectric material 22 and a top side electrode 28 that is overlaid with a hermeticity layer 32, an interface layer 34, a self-assembled monolayer 36, and a functionalization (e.g., specific binding) material 38. In certain embodiments, the MEMS resonator device includes a bulk acoustic wave resonator device, and the piezoelectric material 22 comprises aluminum nitride or zinc oxide material that includes a c-axis having an orientation distribution that is predominantly non-parallel (and may also be non-perpendicular) to normal of a face of the substrate (not shown in FIG. 2). Such a c-axis orientation distribution enables creation of shear displacements, which beneficially enable operation of the MEMS resonator device with liquids, such as in a sensor and/or microfluidic device. In certain embodiments, the piezoelectric material includes a c-axis with a longitudinal orientation.

Methods for forming hexagonal crystal structure piezoelectric materials including a c-axis having an orientation distribution that is predominantly non-parallel to normal of a face of a substrate are disclosed in U.S. patent application Ser. No. 15/293,063 filed on Oct. 13, 2016, with the foregoing application hereby being incorporated by reference herein. Additional methods for forming piezoelectric materials having an inclined c-axis orientation are disclosed in U.S. Pat. No. 4,640,756 issued on Feb. 3, 1987, with the foregoing patent hereby being incorporated by reference herein.

Certain embodiments are directed to a fluidic device including a bulk acoustic wave MEMS resonator device as disclosed herein and including a fluidic passage (e.g., a channel, a chamber, or the like) arranged to conduct a liquid to contact at least one functionalization (e.g., specific binding) material. Such a device may be microfluidic in scale, and comprise at least one microfluidic channel (e.g., having at least one dimension, such as height and/or width, of no greater than about 500 microns, or about 250 microns, or about 100 microns). For example, following fabrication of a bulk acoustic wave MEMS resonator device and deposition of an interface layer and a SAM over portions thereof (optionally preceded by deposition of a hermeticity layer), a microfluidic device may be fabricated by forming one or more walls defining lateral boundaries of a microfluidic channel preferably containing the active region of at least one acoustic resonator, followed by application of a cover or cap layer to enclose the microfluidic channel. In certain embodiments, functionalization (e.g., specific binding) material may be applied after formation of walls of a microfluidic channel, but prior to application of the cover or cap layer. Walls of a microfluidic channel may be formed of any suitable material, such as laser-cut "stencil" layers of thin polymeric materials and/or laminates, optionally including one or more self-adhesive surfaces (e.g., adhesive tape). Optionally such walls may be formed prior to deposition of a SAM, functionalization material, and/or blocking layers, with an SU-8 negative epoxy resist or other photoresist material. In certain embodiments, a cover or cap layer may be integrally formed with one or more walls (e.g., via molding or another suitable process) to define upper and lateral boundaries of at least one fluidic channel, and the integrally formed cover/wall structure may be applied (e.g., adhered or otherwise bonded) over at least a portion of a bulk acoustic wave resonator structure to enclose the at least one fluidic channel. In certain embodiments, functionalization (e.g., specific binding) material may be pre-applied to the active region of a bulk acoustic wave resonator structure before formation of a microfluidic passage; in other embodiments, functionalization material may be applied over an active region of a bulk acoustic wave resonator structure following formation of the microfluidic passage.

In certain embodiments, a chemical or biological blocking material may be applied over a portion of a SAM to prevent attachment of a functionalization (e.g., specific binding) material over one or more selected regions of a BAW resonator structure (e.g., one or more regions apart from an active region). The proper choice of a chemical or biological blocking material (e.g., blocking buffer) for a given analysis depends on the type of target species or analyte present in a sample. Various types of blocking buffers such as highly purified proteins, serum, or milk may be used to block free sites on a SAM. Additional blockers include ethanolamine or polyethylene oxide (PEO) containing materials. An ideal blocking buffer would bind to all potential sites of nonspecific interaction away from an active region. To optimize a blocking buffer for a particular analysis, empirical testing may be used to determine signal-to-noise ratio. No single chemical blocking material is ideal for every situation, since each antibody-antigen pair has unique characteristics.

Figure 3:
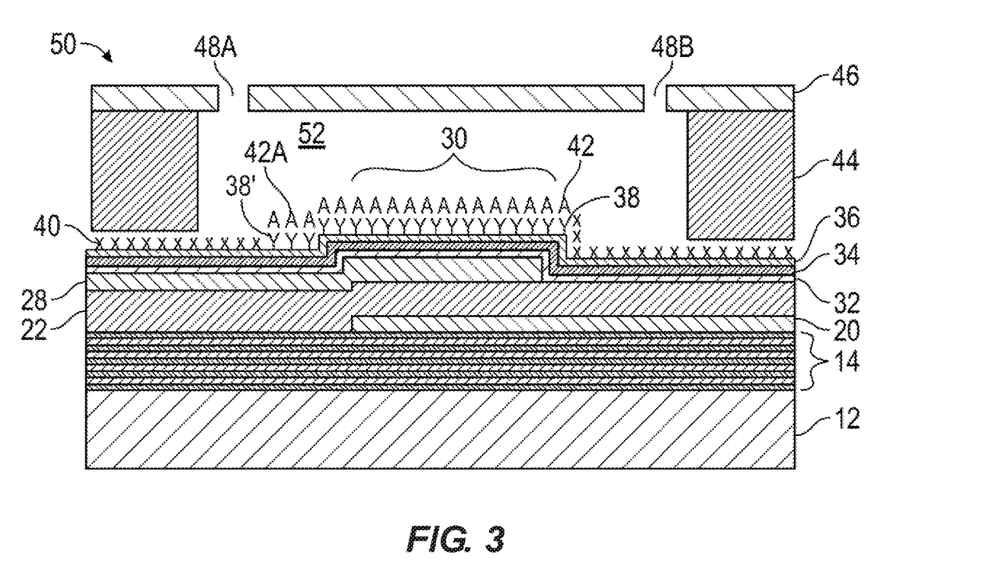
FIG. 3 is a schematic cross-sectional view of a portion of a fluidic device (e.g., a biochemical sensor device) including a microfluidic channel bounded from below by a bulk acoustic wave (BAW) resonator structure, bounded laterally by walls, and bounded from above by a cover defining fluidic ports arranged along an upper or top surface of the fluidic device, to serve as a comparison device intended to provide context for subsequently described embodiments of the present disclosure.

FIG. 3 is a schematic cross-sectional view of a portion of a fluidic device 50 (e.g., a biochemical sensor device) including a microfluidic channel 52 bounded from below by a bulk acoustic wave (BAW) resonator structure, bounded laterally by walls 44, and bounded from above by a cover or cap layer 46 defining upper or top surface fluidic ports 48A, 48B, with the fluidic device 50 serving as a comparison device intended to provide context for subsequently-described embodiments of the present disclosure. The fluidic device 50 includes a substrate 12 overlaid with an acoustic reflector 14, and a bottom side electrode 20 arranged generally below a piezoelectric material 22. A top side electrode 28 extends over a portion of the piezoelectric material 22, wherein a portion of the piezoelectric material 22 arranged between the top side electrode 28 and the bottom side electrode 20 embodies an active region 30 of the BAW resonator structure. The top side electrode 28 and the piezoelectric material 22 are overlaid with a hermeticity layer 32, an interface layer 34, and a self-assembled monolayer (SAM) 36. Portions of the SAM 36 extending away from the active region 30 are overlaid with a chemical or biological blocking material 40 to prevent attachment of specific binding material. A portion of the SAM 36 registered with the active region 30 is overlaid with functionalization (e.g., specific binding) material 38 arranged to bind a specified analyte. Walls 44 that are laterally displaced from the active region 30 extend upward from the chemical or biological blocking material 40 to define lateral boundaries of the microfluidic channel 52 containing the active region 30. Such walls 44 may be formed of any suitable material, such as a laser-cut "stencil" layer of thin polymeric materials and/or laminate materials, optionally including one or more self-adhesive surfaces (e.g. adhesive tape). Optionally such walls 44 may be formed prior to deposition of the SAM 36, functionalization material 38, and chemical or biological blocking material 40 with an SU-8 negative epoxy resist or other photoresist material. If the walls 44 are formed on the SAM 36, the SAM 36 may promote adhesion of the walls 44. The cover or cap layer 46 defining upper surface fluidic ports 48A, 48B is further provided to provide an upper boundary for the microfluidic channel 52. The cover or cap layer 46 may be formed by defining ports (e.g., via laser cutting or water jet cutting) in a layer of an appropriate material (e.g., a substantially inert polymer, glass, silicon, ceramic, or the like), and adhering the cover or cap layer 46 to top surfaces of the walls 44.

In use of the fluidic device 50, a fluid sample may be supplied through the first upper surface fluidic port 48A, into the microfluidic channel 52 over the active region 30, and through the second upper surface fluidic port 48B to exit the microfluidic channel 52. As shown in FIG. 3, an analyte 42 supplied by the fluid sample is bound to the functionalization (e.g., specific binding) material 38. When a bulk acoustic wave is induced in the active region 30 by supplying an electrical (e.g., alternating current) signal to the bottom and top side electrodes 20, 28, detection of a change in at least one of a frequency property, a magnitude property, or a phase property of the bulk acoustic wave resonator structure indicates a presence and/or quantity of target species (i.e., analyte) bound to the functionalization material 38. Electrical connections (e.g., bond pads, not shown) are typically arranged at or along an upper surface of the fluidic device 50 (e.g., above the piezoelectric material 22). Owing to the presence of upper surface fluidic ports 48A, 48B and electrical connections at or along an upper or topside surface of the fluidic device 50, such elements must be separated from one another for packaging reasons and to avoid undesirable contact between fluids and electrical connections.

Figure 4:
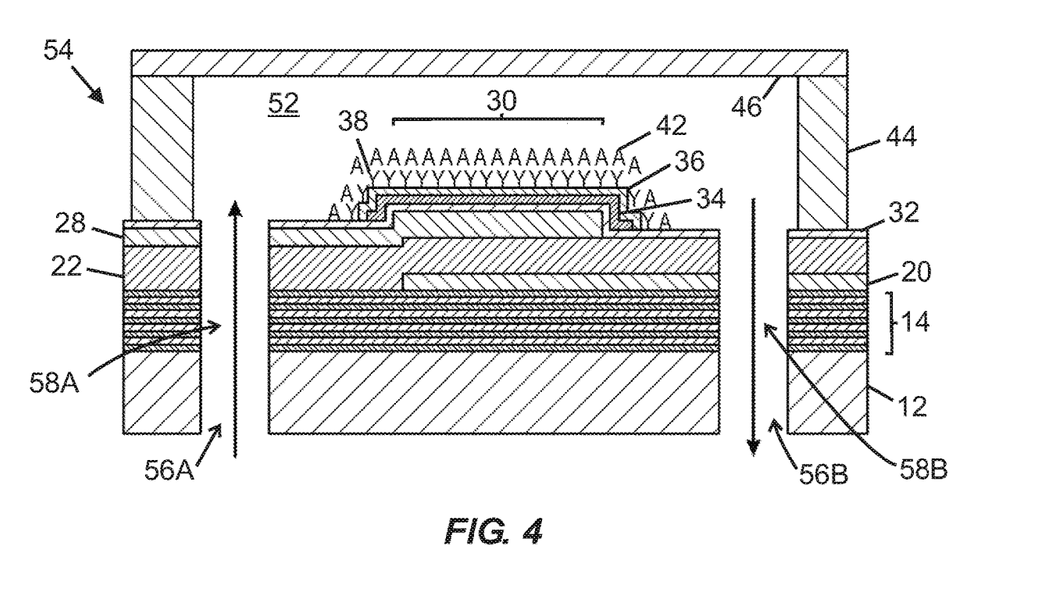
FIG. 4 is a schematic cross-sectional view of a portion of a fluidic device (e.g., a biochemical sensor device) including a microfluidic channel bounded from below by a BAW resonator structure, with fluidic vias extending through a substrate supporting the BAW resonator structure to enable fluid to be supplied from a bottom side of the fluidic device to the microfluidic channel.

FIG. 4 is a schematic cross-sectional view of a portion of a fluidic device 54 according to one embodiment of the present disclosure, including fluidic inlet and outlet vias 58A, 58B extending through a substrate 12 supporting a bulk acoustic wave (BAW) resonator structure to enable fluid to be supplied from a bottom side of the fluidic device 54 to a microfluidic channel 52 overlying an active region 30. Starting from the bottom of the fluidic device 54, the substrate 12 (e.g., silicon or another semiconductor material), is overlaid in sequence with an acoustic reflector 14, a bottom side electrode 20, a piezoelectric material 22, and a top side electrode 28 to provide a bulk acoustic wave (BAW) resonator structure. An area in which the piezoelectric material 22 is arranged between overlapping portions of the top side electrode 28 and the bottom side electrode 20 embodies the active region 30 of the BAW resonator structure. The piezoelectric material 22 and the top side electrode 28 are overlaid with a hermeticity layer 32. A central portion of the hermeticity layer 32 registered with the active region 30 is overlaid with an interface layer 34, a self-assembled monolayer (SAM) 36, and a functionalization (e.g., specific binding) material 38. The BAW resonator structure and the foregoing overlying layers (i.e., hermeticity layer 32, interface layer 34, SAM 36, and functionalization material 38) define a lower boundary of the microfluidic channel 52 containing the active region 30. Walls 44 that are laterally displaced from the active region 30 extend upward from the hermeticity layer 32 to define lateral boundaries of the microfluidic channel 52. A cover or cap layer 46 affixed to the walls 44 is further provided to serve as an upper boundary of the microfluidic channel 52. In certain embodiments, the cover or cap layer 46 may be integrally formed with the walls 44 (e.g., via molding or another suitable technique).

A fluid inlet port 56A and fluid outlet port 56B are defined in a bottom surface of the substrate 12. The fluid inlet port 56A is in fluid communication with the fluidic inlet via 58A, and the fluid outlet port 56B is in fluid communication with the fluidic outlet via 58B. The fluidic inlet and outlet vias 58A, 58B extend through the substrate 12, acoustic reflector 14, piezoelectric material 22, and bottom and/or top side electrodes 20, 28, such that the fluidic inlet via 58A is in fluid communication with a first end of the microfluidic channel 52, and the fluidic outlet via 58B is in fluid communication with a second end of the microfluidic channel 52. The active region 30 is positioned within the microfluidic channel 52. In certain embodiments, each fluid port 56A, 56B forms an aperture (e.g., a circular opening) in the bottom surface of the substrate 12, and each fluidic via 58A, 58B forms a conduit (e.g., a cylindrical passage) through the substrate 12 and overlying layers.

In use of the fluidic device 54, a fluid sample may be supplied through the fluid inlet port 56A and the fluidic inlet via 58A into the microfluidic channel 52, over and past the active region 30, and through the fluidic outlet via 58B and fluid outlet port 56B to exit the microfluidic channel 52. As shown in FIG. 4, an analyte 42 supplied by the fluid sample is bound to the functionalization (e.g., specific binding) material 38. The fluidic device 54 may be used as a sensor to detect presence of a target species in an environment. When a bulk acoustic wave is induced in the active region 30 by supplying an electrical signal (e.g., a radio frequency alternating current signal configured to drive the piezoelectric material 22 in a shear mode) to the bottom and top side electrodes 20, 28, detection of a change in at least one of a frequency property, a magnitude property, or a phase property of the BAW resonator structure indicates a presence and/or quantity of target species (i.e., analyte) bound to the functionalization material 38. For example, mass loading due to binding of analyte 42 to the functionalization material 38 may be detected by a shift in resonant frequency of the BAW resonator structure. Electrical connections (e.g., bond pads, not shown) may be arranged at or along an upper surface of the fluidic device 54 (e.g., above the piezoelectric material 22), opposing the fluid inlet and outlet ports 56A, 56B arranged along a lower surface of the fluidic device 54. Since they are provided along opposing top and bottom surfaces of the fluidic device 54, the electrical connections and the fluidic connections are isolated from one another, and packaging constraints are reduced.

In the fluidic device 54 illustrated in FIG. 4, the interface layer 34, SAM 36, and functionalization material 38 cover the entire active region 30. In alternative embodiments, an interface layer, a SAM, and functionalization material may be arranged over less than an entirety of an active region. For example, in certain embodiments, a patterned blocking layer (e.g., including one or more non-oxide thin films such as silicon nitride [$Si_3N_4$] or silicon carbide [SiC]; or organic materials such as SU-8, photoresist, polyimide, parylene, or poly(ethylene glycol)) may be arranged over at least a portion of an interface layer, whereby presence of the patterned blocking material renders a portion of the interface layer unavailable to receive a SAM.

Figure 5A:
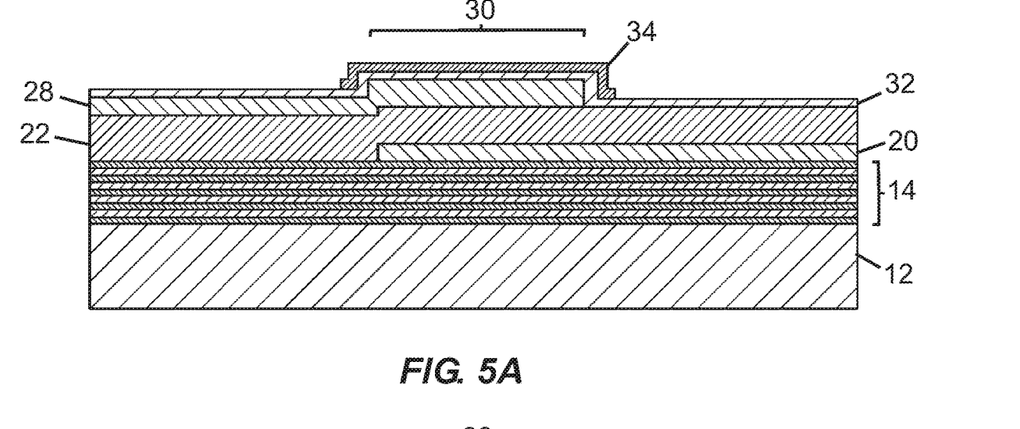
FIG. 5A is a schematic cross-sectional view of the MEMS resonator device portion of FIG. 1 following application of a hermeticity layer and an interface layer over the top side electrode and the piezoelectric material, as a step in fabricating the fluidic device of FIG. 4.

FIGS. 5A-5D illustrate steps for forming the BAW sensor of FIG. 4. More specifically, FIG. 5A is a schematic cross-sectional view illustrating the MEMS resonator device portion of FIG. 1 following application of a hermeticity layer 32 over the top side electrode 28 and the piezoelectric material 22, and following application of an interface layer 34 over a portion of the hermeticity layer 32 registered with an active region 30. In certain embodiments, the hermeticity layer 32 consists of or includes aluminum oxide ($Al_2O_3$) film and/or the interface layer 34 consists of or includes silicon dioxide ($SiO_2$), titanium dioxide ($TiO_2$), or hafnium oxide ($HfO_2$). In certain embodiments, the hermeticity layer 32 and/or interface layer 34 may be applied by atomic layer deposition (ALD) and/or chemical vapor deposition (CVD). As noted previously herein, the hermeticity layer 32 preferably serves as a passivation and moisture barrier layer, and the interface layer 34 serves as an adhesion layer for subsequent fixation of a SAM thereto.

Figure 5B:
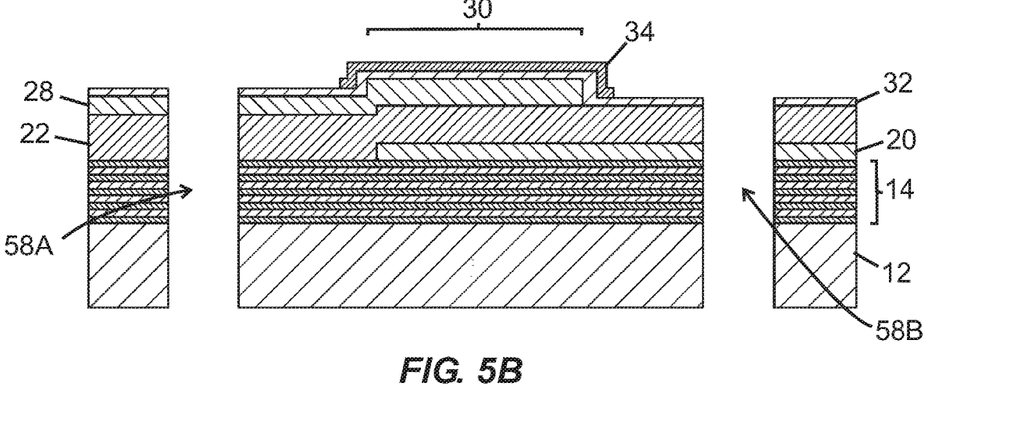
FIG. 5B is a schematic cross-sectional view illustrating the MEMS resonator device portion of FIG. 5A following formation of fluidic vias through the substrate, acoustic reflector, piezoelectric material, electrodes, and hermeticity layer as another step in fabricating the fluidic device of FIG. 4.

FIG. 5B is a schematic cross-sectional view illustrating the MEMS resonator device portion of FIG. 5A following formation of fluidic inlet and outlet vias 58A, 58B through the substrate 12, acoustic reflector 14, piezoelectric material 22, bottom and top side electrodes 20, 28, and hermeticity layer 32 as another step in fabricating the fluidic device of FIG. 4. In certain embodiments, the fluidic inlet and outlet vias 58A, 58B may be formed by laser micromachining guided by a water jet, deep reactive-ion etching (DRIE), laser micromachining, chemical dry etching, chemical wet etching, abrasive jet machining, a combination of two or more of the foregoing processes, or any other suitable tool or method. In certain embodiments, a Synova laser microjet (Synova S. A., Lausanne, Switzerland) may be used, in which a waterjet guides a laser to ablate and melt the substrate 12, acoustic reflector 14, bottom and top side electrodes 20, 28, and/or piezoelectric material 22. In certain embodiments, photoresist may be applied on the upper or front side of the subassembly (e.g., over the hermeticity layer 32 and interface layer 34) for temporary protection during formation of the fluidic inlet and outlet vias 58A, 58B.

Figure 5C:
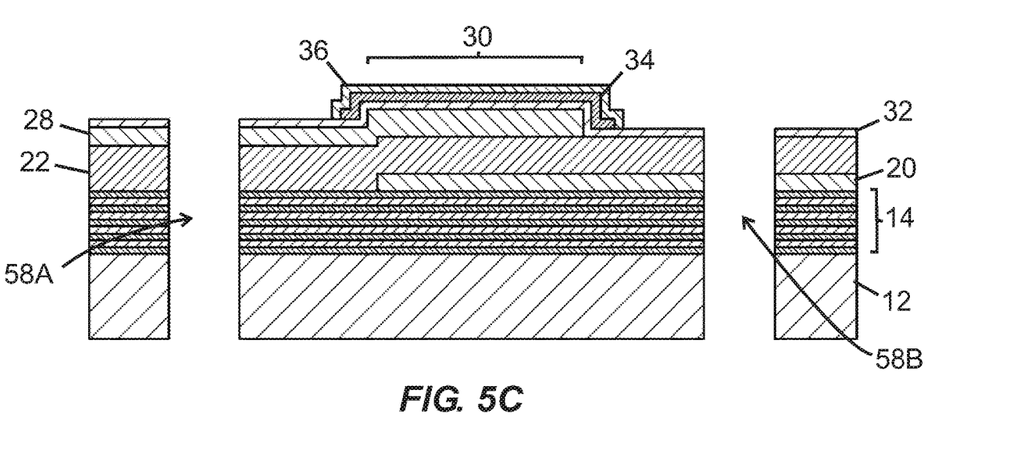
FIG. 5C is a schematic cross-sectional view illustrating the MEMS resonator device portion of FIG. 5B following formation of a self-assembled monolayer (SAM) over an active region, as another step in fabricating the fluidic device of FIG. 4.
Figure 5D:
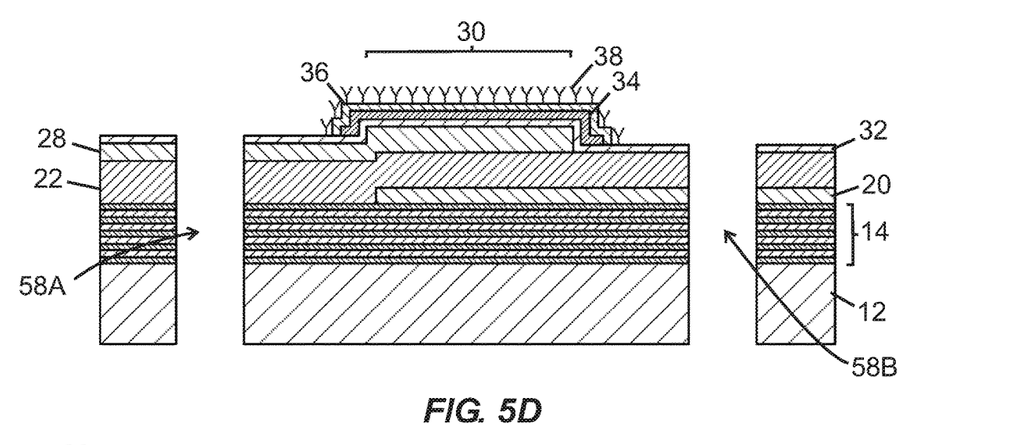
FIG. 5D is a schematic cross-sectional view illustrating the MEMS resonator device portion of FIG. 5C following application of a functionalization (e.g., specific binding) material over the SAM, as additional steps in fabricating the fluidic device of FIG. 4.

FIG. 5C is a schematic cross-sectional view illustrating the MEMS resonator device portion of FIG. 5B following formation of a self-assembled monolayer (SAM) 36 over the interface layer 34 (e.g., patterned ALD $SiO_2$), and FIG. 5D is a schematic cross-sectional view illustrating the MEMS resonator device portion of FIG. 5C following application of functionalization (e.g., specific binding) material 38 over the SAM 36, as additional steps in fabrication of the fluidic device of FIG. 4. The SAM 36 is applied to promote bonding or adhesion of the functionalization material 38. In certain embodiments, the SAM 36 may comprise an organosilane material (e.g., 3-glycidoxypropyltrimethoxysilane), and the interface layer 34 may comprise patterned $SiO_2$. In certain embodiments, the functionalization material 38 (e.g., antibodies) may be printed with a microarray spotting needle, and adhere only to regions where the SAM 36 is present, and any unbound excess functionalization material 38 may be washed away. In certain embodiments, regions of the SAM 36 on which no functionalization is desired or present may be chemically or biologically blocked to prevent application of functionalization material 38 to undesired portions of the SAM 36, or to prevent undesired non-specific binding of one or more chemical species to the SAM 36 during operation of the fluidic device. To complete formation of the fluidic device 54 shown in FIG. 4, walls and a cover or cap layer (not shown) may be applied over regions of the hermeticity layer 32 laterally spaced from the active region 30, and the fluidic inlet and outlet vias 58A, 58B define a microfluidic channel (not shown). In certain embodiments, the walls and cover or cap layer may be precut with a laser, or defined by molding, and then applied to the hermeticity layer 32 with a pressure-sensitive adhesive or other suitable attachment means.

Figure 6:
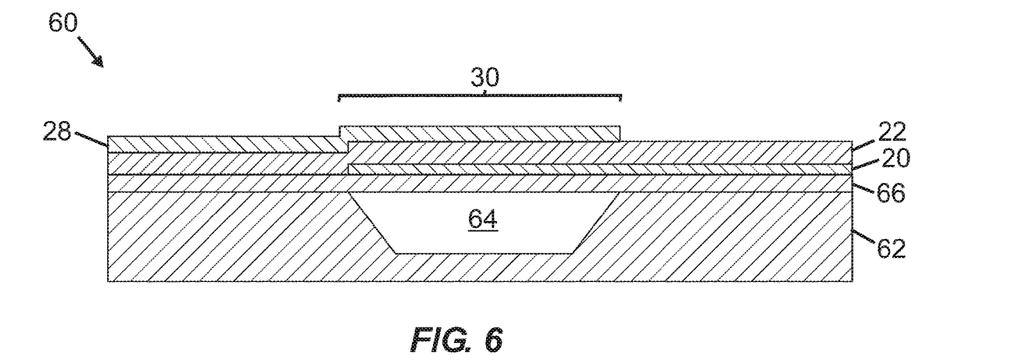
FIG. 6 is a schematic cross-sectional view of a film bulk acoustic wave resonator (FBAR) structure useable in fluidic devices according to certain embodiments, with the FBAR structure including an inclined c-axis hexagonal crystal structure piezoelectric material, a substrate defining a cavity covered by a support layer, and an active region registered with the cavity with a portion of the piezoelectric material arranged between overlapping portions of a top side electrode and a bottom side electrode.

FIG. 6 is a schematic cross-sectional view of a film bulk acoustic wave resonator (FBAR) structure 60 according to one embodiment including an inclined c-axis hexagonal crystal structure piezoelectric material bulk layer (e.g., piezoelectric material) 22. The FBAR structure 60 includes a substrate 62 (e.g., silicon or another semiconductor material) defining a cavity 64 covered by a support layer 66 (e.g., silicon dioxide), and includes an active region 30 registered with the cavity 64 with a portion of the piezoelectric material 22 arranged between overlapping portions of a top side electrode 28 and a bottom side electrode 20. The bottom side electrode 20 is arranged over the cavity 64 with the support layer 66 arranged therebetween. In certain embodiments, the support layer 66 may be removed or omitted. The bottom side electrode 20 and the support layer 66 are overlaid with the piezoelectric material 22 embodying inclined c-axis hexagonal crystal structure piezoelectric material (e.g., AlN or ZnO) and the top side electrode 28 is arranged over at least a portion of a top surface of the piezoelectric material 22. A portion of the piezoelectric material 22 arranged between the top side electrode 28 and the bottom side electrode 20 embodies the active region 30 of the FBAR structure 60. The active region 30 is arranged over and registered with the cavity 64 disposed below the support layer 66. The cavity 64 serves to confine acoustic waves induced in the active region 30 by preventing dissipation of acoustic energy into the substrate 62, since acoustic waves do not efficiently propagate across the cavity 64. In this respect, the cavity 64 provides an alternative to the acoustic reflector discussed above in connection with FIG. 4. As noted above, the support layer 66 may be optional in certain embodiments. Although the cavity 64 shown is bounded from below by a thinned portion of the substrate 62, in alternative embodiments at least a portion of the cavity 64 extends through an entire thickness of the substrate 62. Steps for forming the FBAR structure 60 may include defining the cavity 64 in the substrate 62, filling the cavity 64 with a sacrificial material (not shown), optionally followed by planarization of the sacrificial material, depositing the support layer 66 over the substrate 62 and the sacrificial material, removing the sacrificial material (e.g., by flowing an etchant through vertical openings defined in the substrate 62 or the support layer 66, or lateral edges of the substrate 62), depositing the bottom side electrode 20 over the support layer 66, growing (e.g., via sputtering or other appropriate methods) the piezoelectric material 22, and depositing the top side electrode 28.

Figure 7:
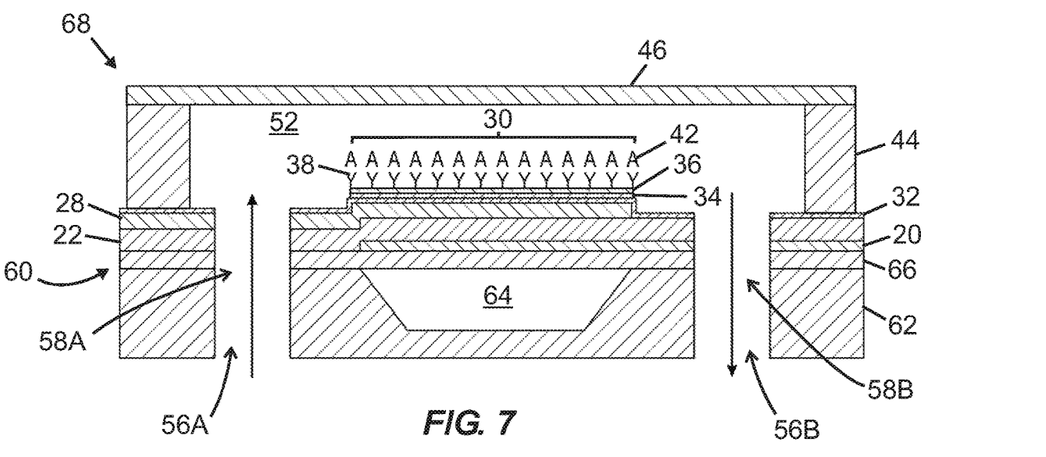
FIG. 7 is a schematic cross-sectional view of a fluidic device incorporating the FBAR structure of FIG. 6, with backside fluidic vias extending through a substrate of the FBAR structure, and with the active region of the FBAR structure overlaid with a hermeticity layer, an interface layer, and a functionalization (e.g., specific binding) material.

FIG. 7 is a schematic cross-sectional view of a fluidic device 68 incorporating the FBAR structure 60 of FIG. 6, with fluidic inlet and outlet vias 58A, 58B extending through a substrate 62 of the FBAR structure 60 to permit fluid communication with a microfluidic channel 52 containing the active region 30 of the FBAR structure 60. The fluidic device 68 includes many of the same features and elements of the fluidic device described in connection with FIG. 4 and operates similarly thereto, except that a cavity 64 is used instead of an acoustic reflector 14 to confine an acoustic wave in or along the piezoelectric material 22 to prevent dissipation of acoustic energy in the substrate 62. The cavity 64 defined in the substrate 62 is bounded by a support layer 66, which is overlaid in sequence with a bottom side electrode 20, the piezoelectric material 22, and a top side electrode 28. An area in which the piezoelectric material 22 is arranged between overlapping portions of the top side electrode 28 and the bottom side electrode 20 embodies the active region 30 of the FBAR structure 60. The piezoelectric material 22 and the top side electrode 28 are overlaid with a hermeticity layer 32. A central portion of the hermeticity layer 32 registered with the active region 30 is overlaid with an interface layer 34, a self-assembled monolayer (SAM) 36, and a functionalization (e.g., specific binding) material 38. Walls 44 that are laterally displaced from the active region 30 extend upward from the hermeticity layer 32 to define lateral boundaries of the microfluidic channel 52, and a cover or cap layer 46 defines an upper boundary of the microfluidic channel 52.

A fluid inlet port 56A and fluid outlet port 56B are defined in a bottom surface of the substrate 62. The fluid inlet port 56A is in fluid communication with the fluidic inlet via 58A, and the fluid outlet port 56B is in fluid communication with the fluidic outlet via 58B. The fluidic inlet and outlet vias 58A, 58B extend through the substrate 62, the support layer 66, the piezoelectric material 22, and the bottom and/or top side electrodes 20, 28, such that the fluidic inlet via 58A is in fluid communication with a first end of the microfluidic channel 52, and the fluidic outlet via 58B is in fluid communication with a second end of the microfluidic channel 52. The active region 30 is positioned within the microfluidic channel 52.

In use of the fluidic device 68, a fluid sample may be supplied through the fluid inlet port 56A and the fluidic inlet via 58A into the microfluidic channel 52, over and past the active region 30, and through the fluidic outlet via 58B and fluid outlet port 56B to exit the microfluidic channel 52. As shown in FIG. 7, an analyte 42 supplied by the fluid sample is bound to the functionalization (e.g., specific binding) material 38. The fluidic device 68 may be used as a sensor to detect presence of a target species in an environment. When a bulk acoustic wave is induced in the active region 30 by supplying an electrical signal (e.g., a radio frequency alternating current signal configured to drive the piezoelectric material 22 in a shear mode) to the bottom and top side electrodes 20, 28, detection of a change in at least one of a frequency property or a phase property of the FBAR structure 60 indicates a presence and/or quantity of target species (i.e., analyte) bound to the functionalization material 38.

Figure 8:
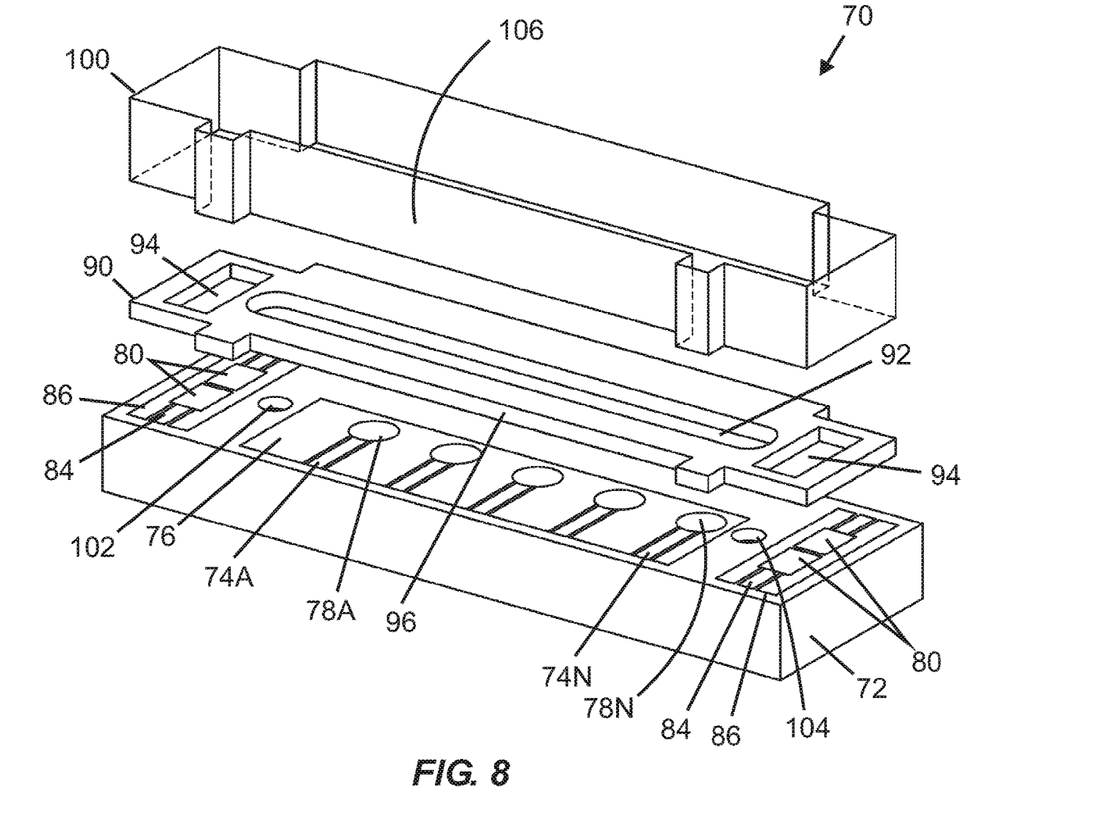
FIG. 8 is a perspective assembly view of a microfluidic device incorporating a substrate with multiple bulk acoustic wave MEMS resonator devices as disclosed herein, an intermediate layer defining a channel containing active regions of the MEMS resonator devices, and a cover or cap layer, with fluidic vias defined through the substrate.

FIG. 8 is a perspective assembly view of a microfluidic device 70 incorporating a substrate 72 with multiple bulk acoustic wave MEMS resonator devices, an intermediate layer 90 defining a central microfluidic channel 92 registered with active regions 78A-78N of the MEMS resonator devices, and a cover or cap layer 100 arranged to cover the intermediate layer 90. Top central portions of the substrate 72, which includes an acoustic reflector (not shown) and a piezoelectric material (not shown), include a top side electrode 76 and bottom side electrode pads 74A-74N. Regions in which the foregoing electrodes overlap one another and sandwich the piezoelectric material embody active regions 78A-78N. Any suitable number of active regions 78A-78N may be provided and fluidically arranged in series or parallel, although five active regions arranged in series are illustrated in FIG. 8. Top peripheral (or top end) portions of the substrate 72 further include reference top side electrodes 86 and reference bottom side electrodes 84 in communication with reference overlap regions 80. Such reference overlap regions 80 are not exposed to fluid, and are present to provide a basis for comparing signals obtained from the active regions 78A-78N exposed to fluid within the central microfluidic channel 92. The substrate 72 further includes fluidic vias 102, 104 extending between a bottom surface of the substrate 72 and the central microfluidic channel 92. Each fluidic via 102, 104 extends between a microfluidic port accessible along a bottom surface of the substrate 72 and an opening along a top surface of the substrate 72. The substrate 72 is overlaid with the intermediate (e.g., wall-defining) layer 90, wherein the central microfluidic channel 92 is intended to receive fluid, and defines peripheral chambers 94 arranged to overlie the reference overlap regions 80 in a sealed fashion. The intermediate layer 90 may be formed of any suitable material such as SU-8 negative epoxy resist, other photoresist material, or laser-cut "stencil" layers of thin polymeric materials optionally including one or more self-adhesive surfaces (e.g., adhesive tape), etc. The intermediate layer 90 further includes a lateral inset region 96 that enables lateral portions of the top side electrode 76 and bottom side electrode pads 74A-74N to be accessed upon assembly of the microfluidic device 70. The cover or cap layer 100 includes a lateral inset region 106 registered with the lateral inset region 96 of the intermediate layer 90. Top openings of the fluidic vias 102, 104 are registered with end portions of the central microfluidic channel 92 defined in the intermediate layer 90 to permit fluid (e.g., liquid) to be supplied to the central microfluidic channel 92 over the active regions 78A-78N.

Preferably, at least the active regions 78A-78N are overlaid with a hermeticity layer, an interface layer, a self-assembled monolayer, and functionalization (e.g., specific binding) material as disclosed herein. Microfluidic devices according to other configurations may be provided, as will be recognized by those skilled in the art upon review of the present disclosure.

Those skilled in the art will recognize improvements and modifications to the preferred embodiments of the present disclosure. All such improvements and modifications are considered within the scope of the concepts disclosed herein and the claims that follow.

What is claimed is:

1. A fluidic device comprising:
  a base structure comprising: (i) a substrate; (ii) at least one bulk acoustic wave resonator structure arranged over at least a portion of the substrate, the at least one bulk acoustic wave resonator structure including a piezoelectric material comprising a c-axis having an orientation distribution that is predominantly non-parallel to normal of a face of the substrate, a top side electrode arranged over a portion of the piezoelectric material, and a bottom side electrode arranged between the piezoelectric material and the substrate, wherein a portion of the piezoelectric material is arranged between the top side electrode and the bottom side electrode to form an active region; and (iii) a functionalization material arranged over at least a portion of the active region;
  a fluidic channel bounded at least in part by the base structure;
  at least one fluidic via defined through at least a portion of the base structure including the substrate and in fluid communication with the fluidic channel, wherein the at least one fluidic via extends through the substrate and a thickness of the piezoelectric material, and
  wherein the fluidic device has a first surface and a second surface different than the first surface, where the first surface is configured to receive an electrical connection for conductive electrical communication with one or both of the top side electrode and the bottom side electrode, and the second surface defines a fluid port in fluid communication with the fluidic via.

2. The fluidic device of claim 1, wherein the base structure further comprises a self-assembled monolayer arranged over the active region, wherein the functionalization material comprises a specific binding material arranged over the self-assembled monolayer.

3. The fluidic device of claim 2, wherein the base structure further comprises an interface layer arranged over at least a portion of the active region, and the self-assembled monolayer is arranged over at least a portion of the interface layer.

4. The fluidic device of claim 3, wherein the interface layer extends over less than an entirety of the piezoelectric material.

5. The fluidic device of claim 3, wherein the top side electrode comprises a non-noble metal, and the fluidic device further comprises a hermeticity layer arranged between the interface layer and the top side electrode.

6. The fluidic device of claim 1, further comprising at least one channel boundary-defining structure arranged over the base structure, wherein the at least one channel boundary-defining structure defines an upper boundary and at least one lateral boundary of the fluidic channel.

7. The fluidic device of claim 6, wherein the at least one channel boundary-defining structure comprises at least one intermediate structure defining the at least one lateral boundary of the fluidic channel, and comprises a cover defining the upper boundary of the fluidic channel.

8. The fluidic device of claim 1, wherein the at least one fluidic via comprises a plurality of fluidic vias defined through the at least a portion of the base structure.

9. The fluidic device of claim 1, wherein the base structure further comprises an acoustic reflector structure arranged between the substrate and the bottom side electrode.

10. The fluidic device of claim 1, wherein the substrate defines a recess underlying the bottom side electrode and proximate to the active region.

11. The fluidic device of claim 1, wherein the at least one bulk acoustic wave resonator structure comprises a plurality of bulk acoustic wave resonator structures registered with the fluidic channel.

12. The fluidic device of claim 1, wherein the functionalization material comprises a non-specific binding material.

13. The fluidic device of claim 1, further comprising:
  a top side arranged closer to the piezoelectric material than to the substrate; and
  a bottom side arranged closer to the substrate than to the piezoelectric material;
  wherein the electrical connection comprises a first electrical bond pad and a second electrical bond pad arranged along the top side, wherein the first electrical bond pad is in conductive electrical communication with the top side electrode, and the second electrical bond pad is in conductive electrical communication with the bottom side electrode;

wherein the at least one fluidic via extends through the bottom side.

14. A method for biological or chemical sensing, the method comprising:
supplying a fluid containing a target species through the at least one fluidic via into the fluidic channel of the fluidic device according to claim 1, wherein said supplying is configured to cause at least some of the target species to bind to the functionalization material;
inducing a bulk acoustic wave in the active region; and
sensing a change in at least one of a frequency property, a magnitude property, or a phase property of the at least one bulk acoustic wave resonator structure to indicate at least one of presence or quantity of target species bound to the functionalization material.

15. A method for fabricating a fluidic device comprising at least one bulk acoustic wave resonator structure arranged over at least a portion of a substrate, the at least one bulk acoustic wave resonator structure including a piezoelectric material comprising a c-axis having an orientation distribution that is predominantly non-parallel to normal of a face of the substrate, a top side electrode arranged over a portion of the piezoelectric material, and a bottom side electrode arranged between the piezoelectric material and the substrate, wherein a portion of the piezoelectric material is arranged between the top side electrode and the bottom side electrode to form an active region, the method comprising:
defining at least one fluidic via through the substrate and a thickness of the piezoelectric material;
providing at least one functionalization material over at least a portion of the active region; and
arranging at least one channel boundary-defining structure over the at least one bulk acoustic wave resonator structure, wherein the at least one channel boundary-defining structure defines an upper boundary and at least one lateral boundary of a fluidic channel in fluidic communication with the at least one fluidic via, and the active region is arranged along a portion of a lower boundary of the fluidic channel.

16. The method of claim 15, further comprising forming an interface layer over at least a portion of the active region, forming a self-assembled monolayer over at least a portion of the interface layer, and providing the at least one functionalization material over at least a portion of the self-assembled monolayer, wherein the at least one functionalization material comprises a specific binding material.

17. The method of claim 16, further comprising forming a hermeticity layer over the top side electrode prior to the forming of the interface layer over at least a portion of the active region.

18. The method of claim 15, wherein the defining of the at least one fluidic via through the substrate and the piezoelectric material comprises laser micromachining guided by a water jet, deep reactive-ion etching, laser micromachining, chemical dry etching, chemical wet etching, abrasive jet machining, or a combination of two or more of the foregoing processes.

19. The method of claim 15, wherein the arranging of the at least one channel boundary-defining structure over the at least one bulk acoustic wave resonator structure is performed prior to the providing of the at least one functionalization material over at least a portion of the active region.

* * * * *